(12) United States Patent
First

(10) Patent No.: US 7,429,386 B2
(45) Date of Patent: Sep. 30, 2008

(54) STRETCH MARK TREATMENT

(75) Inventor: Eric R. First, Boston, MA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 10/934,812

(22) Filed: Sep. 3, 2004

(65) Prior Publication Data

US 2006/0051377 A1    Mar. 9, 2006

(51) Int. Cl.
*A61K 39/02* (2006.01)
*A61K 39/00* (2006.01)
*A61K 39/08* (2006.01)
*A61K 38/00* (2006.01)

(52) U.S. Cl. .............. 424/236.1; 424/184.1; 424/234.1; 424/247.1; 530/300; 530/324

(58) Field of Classification Search .............. 424/247.1, 424/239.1, 236.1
See application file for complete search history.

(56) References Cited

U.S. PATENT DOCUMENTS

| | | | | |
|---|---|---|---|---|
| 5,437,291 | A | 8/1995 | Pasricha et al. | 128/898 |
| 5,670,484 | A | 9/1997 | Binder | 514/14 |
| 5,714,468 | A | 2/1998 | Binder | 514/14 |
| 5,766,605 | A | 6/1998 | Sanders et al. | 424/239.1 |
| 5,989,545 | A | 11/1999 | Foster et al. | 424/183.1 |
| 6,063,768 | A | 5/2000 | First | 514/14 |
| 6,113,915 | A | 9/2000 | Aoki et al. | 424/236.1 |
| 6,139,845 | A | 10/2000 | Donovan | 424/236.1 |
| 6,143,306 | A | 11/2000 | Donovan | 424/236.1 |
| 6,261,572 | B1 | 7/2001 | Donovan | 424/239.1 |
| 6,265,379 | B1 | 7/2001 | Donovan | 514/14 |
| 6,299,893 | B1 | 10/2001 | Schwartz et al. | 424/422 |
| 6,306,423 | B1 | 10/2001 | Donovan et al. | 424/423 |
| 6,312,708 | B1 | 11/2001 | Donovan | 424/423 |
| 6,358,917 | B1 * | 3/2002 | Carruthers et al. | 514/2 |
| 6,365,164 | B1 | 4/2002 | Schmidt | 424/239.1 |
| 6,423,319 | B1 | 7/2002 | Brooks et al. | 424/239.1 |
| 6,447,787 | B1 * | 9/2002 | Gassner et al. | 424/247.1 |
| 6,458,365 | B1 | 10/2002 | Aoki et al. | 424/239.1 |
| 6,464,986 | B1 | 10/2002 | Aoki et al. | 424/239.1 |
| 6,623,742 | B2 | 9/2003 | Voet | 424/236.1 |
| 6,667,041 | B2 | 12/2003 | Schmidt | 424/239.1 |
| 6,787,517 | B1 * | 9/2004 | Gil et al. | 514/1 |
| 2002/0081291 | A1 | 6/2002 | Hawrot | 424/94.63 |
| 2003/0224019 | A1 | 12/2003 | O'Brien | 424/239.1 |
| 2004/0009180 | A1 | 1/2004 | Donovan | 424/184.1 |

FOREIGN PATENT DOCUMENTS

| | | |
|---|---|---|
| DE | 198 52 981 | 11/1998 |
| WO | WO 96/33273 | 4/1996 |
| WO | WO 98/07864 | 2/1998 |
| WO | WO 99/17806 | 4/1999 |
| WO | WO 00/10598 | 3/2000 |
| WO | WO 00/15245 | 3/2000 |
| WO | WO 00/57897 | 3/2000 |
| WO | WO 00/74703 | 5/2000 |
| WO | WO 01/21213 | 3/2001 |
| WO | WO 01/70132 A2 | 9/2001 |
| WO | WO 01/70291 A2 | 9/2001 |
| WO | WO 03/011333 | 2/2003 |

OTHER PUBLICATIONS

Zheng et al (Br. Dermatol. Feb. 1985; 112(2):185-93)(Abstract only).*
Webster's II New Riverside University Dictionary, THe Riverside Publishing Company, 1984.*
Hyde (TeensHealth, Nemours Foundation, date reviewed Apr. 2004).*
Brandt et al (Dermatol Clin 22 (2004) 159-166).*
Freund et al (The Journal of Pain, vol. 4, Issue 3, Apr. 2003, pp. 159-165)(Abstract only).*
Keen et al (Plastic and Reconstructive Surgery, Jul. 1994, 94, No. 1, pp. 94-99).*
Aoki, K., et al, *Mechanisms of the antinociceptive effect of subcutaneous Botox: Inhibition of peripheral and central nociceptive processing*, Cephalalgia Sep. 2003;23(7):649.
Andreadis, S., et al., *Keratinocyte growth factor induces hyperproliferation and delays differentiation in a skin equivalent model system*, FASEB J. Apr. 2001;15(6):898-906.
Arredondo, J., et al., *Central role of alpha7 nicotinic receptor in differentiation of the stratified squamous epithelium*, J Cell Biol. Oct. 28, 2002;159(2):325-36.
Asahina A., et al., *Specific induction of cAMP in Langerhans cells by calcitonin gene-related peptide: relevance to functional effects*, Proc Natl Acad Sci U S A. Aug. 29, 2005;92(18):8323-7.
Bigalke, H., et al., *Botulinum A Neurotoxin Inhibits Non-Cholinergic Synaptic Transmission in Mouse Spinal Cord Neurons in Culture*, Brain Research 360;318-324:1985.

(Continued)

*Primary Examiner*—N. M. Minnifield
*Assistant Examiner*—Vanessa L. Ford
(74) *Attorney, Agent, or Firm*—Claude L. Nassif; Stephen Donovan; Martin Voet

(57) ABSTRACT

Methods for treating stretch marks by local administration of a Clostridial toxin, such as a botulinum toxin, to a patient with a stretch mark.

11 Claims, 1 Drawing Sheet

OTHER PUBLICATIONS

Figure 1:
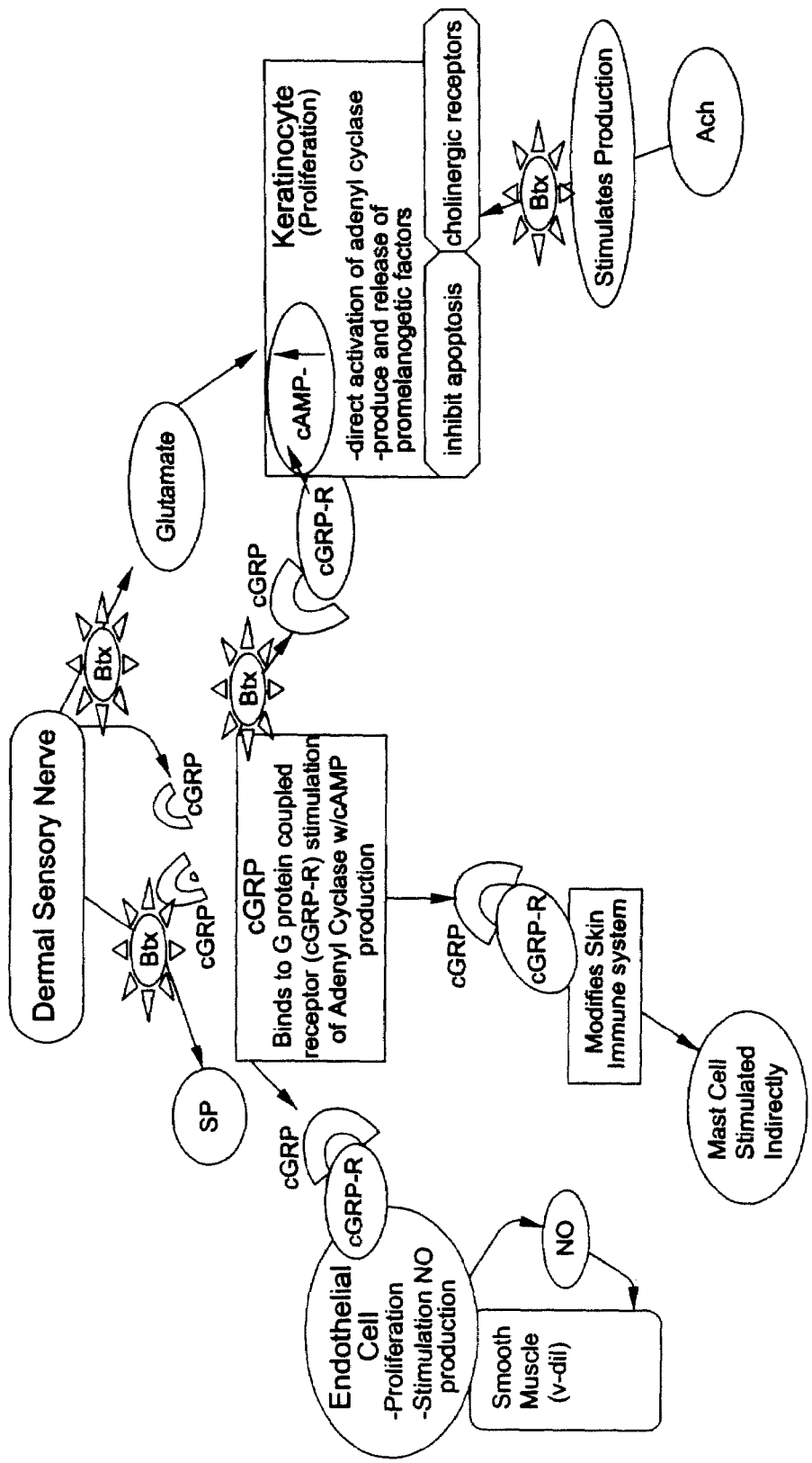

Bigalke, H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316;244-251:1981.

Binz, T. et al., *The Complete Sequence of Botulinum Neurotoxin Type A and Comparison with Other Clostridial Neurotoxins*, J Biological Chemistry 265(16);9153-9158:1990.

Blugerman, G., et al., *Multiple eccrine hidrocystomas: A new therapeutic option with botulinum toxin*, Dermatol Surg May 2003;29(5):557-9.

Borodic et al., *Pharmacology and Histology fo the therapeutic Application of Botulinum Toxin*, Therapy With Botulinum Toxin, Ed. Jankovic, J., et al., Marcel Dekker, Inc., (1994) p. 150.

Brem, H., et al, *Placebo-Controlled Trial of Safety and Efficacy of Intraoperative Controlled Delivery by Biodegradable Polymers of Chemotherapy for Recurrent Gliomas*, Lancet 345;1008-1012:1995.

Bushara, K., *Botulinum toxin and rhinorrhea*, Otolaryngol Head Neck Surg 1996;114(3):507.

Chen, W., et al., *Trophic interactions between sensory nerves and their targets*, Journal of Biomedical Science. 1999;6(2):79-85.

Chiang, H-Y, et al., *Regional difference in epidermal thinning after skin denervation*, Exp Neurol 1998;154(1):137-45.

Chien, Hsiung-F., et al., (2001) *Quantitative pathology of cutaneous nerve terminal degeneration in the human skin*, Acta Neuropathologica 102:455-461.

Childers et al., (2002), American Journal of Physical Medicine & Rehabilitation, 81:751-759.

Coffield et al., *Site and Action of Botulinum Neurotoxin*, Therapy With Botulinum Toxin, Ed. Jankovic, J., et al., Marcel Dekker, Inc., (1994), p. 5.

Dabrowski, E., et al., *Botulinum toxin as a novel treatment for self mutilation in Lesch-Nyhan syndrome*, Ann Neurol Sep. 2002;52(3 Supp 1):S157.

Doggweiler, R., et al., *Botulinum toxin type A causes diffuse and highly selective atrophy of rat prostate*, Neurourol Urodyn 1998;17(4):363.

Fung, L. K. et al., *Pharmacokinetics of Interstitial Delivery of Carmustine 4-Hydroperoxycyclophosphamide and Paclitaxel From a Biodegradable Polymer Implant in the Monkey Brain*, Cancer Research 58; 672-684:1998.

Goldman, (2000), Aesthetic Plastic Surgery Jul.-Aug. 24(4):280-282.

Gonelle-Gispert, Carmen, et al., *SNAP-25a and -25b Isoforms are Both Expressed in Insulin-Secreting Cells and Can Function in Insulin Secretion*, Biochem J. (1999) 339 (pt 1); pp. 159-165.

Grando, S. et al., *Human keratinocytes synthesize, secrete and degrade acetylcholine*, J Invest Dermatol. Jul. 1993;101(1):32-6.

Grando, S., *Biological functions of keratinocyte cholinergic receptors*, J Investig Dermatol Symp Proc. Aug. 1997;2(1):41-8.

Grando, S., et al., *Activation of keratinocyte nicotinic cholinergic receptors stimulates calcium influx and enhances cell differentiation*. Invest Dermatol. Sep. 1996;107(3):412-8.

Grando, S., et al., *Keratinocyte muscarinic acetylcholine receptors: immunolocalization and partial characterization*, J Invest Dermatol. Jan. 1995;104(1):95-100.

Griffin, J., et al., *Axonal degeneration and disorders of the axonal cytoskeleton*. In: Waxman S., et al., *The Axon*. New York: Oxford University Press, 1995:375-390.

Habermann, E., et al., *Tetanus Toxin and Botulinum A and C Neurotoxins Inhibit Noradrenaline Release From Cultured Mouse Brain*, J Neurochem 51(2);522-527:1988.

Habermann, E., *Inhibition by Tetanus and Botulinum A Toxin of the release of [3H]Noradrenaline and [3H]GABA From Rat Brain Homogenate*, Experientia 44;224-226:1988.

Habermann, E., *Naunyn-Schmiedeberg's Arch. Pharmacol.* 1974; 281, 47-56.

*Harrison's Principles of Internal Medicine* (1998), edited by Anthony Fauci et al., 14th edition, published by McGraw Hill.

Heckmann, M., et al., *Botulinum toxin type A injection in the treatment of lichen simplex: An open pilot study*, J Am Acad Dermatol Apr. 2002;46(4):617-9.

Hokfelt, T., *Neuropeptides in perspective : The last ten years*, Neuron 1991; 7: 867-879.

Hosoi, J., et al., *Regulation of Langerhans cell function by nerves containing calcitonin gene-related peptide*, Nature. May 13, 1993;363(6425):159-63.

Hsieh, S., et al., *Epidermal denervation and its effects on keratinocytes and Langerhans cells*, J Neurocytol 1996;25:513-524.

Hsieh, S., et al., *Modulation of keratinocyte proliferation by skin innervation*. Journal of Investigative Dermatology, 1999;113(4):579-86.

Hsieh, S., et al., *Pathology of nerve terminal degeneration in the skin*, Journal of Neuropathology & Experimental Neurology. 2000;59(4):297-307.

Hsieh, S., et al., *Skin innervation and its influence on the epidermis*, J Biomed Sci 1997;4:264-268.

Huang, et al., *Influence of cutaneous nerves on keratinocyte proliferation and epidermal thickness in mice*, Neuroscience. 1999;94(3):965-73.

Inaba, N., et al., *Capsaicin-induced calcitonin gene-related peptide release from isolated rat stomach measured with a new chemiluminescent enzyme immunoassay*, Jpn J Pharmacol. Nov. 1996;72(3):223-9.

Johnson, M., *Synaptic glutamute release by postnatal rat serotonergic neurons in microculture*, Neuron 1994; 12: 433-442.

Jost, W., *Ten years' experience with botulinum toxin in anal fissure*, Int J Colorectal Dis Sep. 2002;17(5):298-302.

Kaneko, T., et al., *Immunohistochemical demonstration of glutaminase in catecholaminergic and serotonergic neurons of rat brain*, Brain Res. 1990; 507: 141-154.

Kasakov, L., et al., *Direct evidence for concomitant release of noradenaline, adenosine 5'-triphosphate and neuropeptide Y from sympathetic nerve supplying the guinea-pig vas deferens*. J. Auton. Nerv. Syst. 1988; 22: 75-82.

Katsambas, A., et al., *Cutaneous diseases of the foot: Unapproved treatments*, Clin Dermatol Nov.-Dec. 2002;20(6):689-699.

Ko, M., et al., *Cutaneous nerve degeneration induced by acrylamide in mice*, Neuroscience Letters.( 2000)293(3):195-8.

Kömuves, Laszlo, et al., *Epidermal expression of the full-length extracellular calcium-sensing receptor is required for normal keratinocyte differentiation*, J Cell Physiol. Jul. 2002;192(1):45-54.

Krnjevic, K., *Central cholinergic mechanisms and function*. Prog Brain Res. 1993;98:285-92.

Kupfermann I., *Functional studies of cotransmission*. Physiol. Rev. 1991; 71: 683-732.48: 545-59.

Lee, M., et al., *Clinical and electrophysiological characteristics of inflammatory demyelinating neuropathies*, Acta Neurol Taiwan 1997;6:283-288.

Legat, F., et al., *Repeated subinflammatory ultraviolet B irradiation increases substance P and calcitonin gene-related peptide content and augments mustard oil-induced neurogenic inflammation in the skin of rats*, Neurosci Lett. Sep. 6, 2002;329(3):309-13.

Li, Y., et al., *Sensory and motor denervation influences epidermal thickness in rat foot glabrous skin*, Exp Neurol 1997;147:452-462 (see p. 459).

Lin, Y., et al., (2001) *Cutaneous nerve terminal degeneration in painful mononeuropathy*, Experimental Neurology. 170(2):290-6.

Lin, Y., et al., *Quantitative sensory testing: normative values and its application in diabetic neuropathy*, Acta Neurol Taiwan 1998;7:176-184.

Lundberg, J., *Pharmacology of cotransmission in the autonomic nervous system: Integrative aspects on amines, neuropeptides, adenosine triphosphate, amino acids and nitric oxide*, Pharmacol. Rev. 1996; 48: 113-178.

Marchese-Ragona, R. et al., *Management of Parotid Sialocele With Botulinum Toxin*, The Laryngoscope 109 (Aug. 1999):1344-1346.

McCarthy, B., et al., *Cutaneous innervation in sensory neuropathies: evaluation by skin biopsy*, Neurol 1995;45:1848-1855.

Movement Disorders, vol. 10, No. 3 (1995), p. 376.

Moyer, E., et al., *Botulinum Toxin Type B: Experimental and Clinical Experience*, being chapter 6, pp. 71-85 of "Therapy With Botulinum Toxin," edited by Jankovic, J. et al. (1994), Marcel Dekker, Inc.

Naumann, Markus, et al., *Botulinum Toxin Type A in the Treatment of Focal, Axillary and Palmar Hyperhidrosis and Other Hyperhidrotic Conditions*, European J. Neurology 6 (Supp 4): S111-S115:1999.

Ndoye, A., et al., *Identification and mapping of keratinocyte muscarinic acetylcholine receptor subtypes in human epidermis*, J Invest Dermatol. Sep. 1998;111(3):410-6.

Nguyen, V., et a., *Keratinocyte acetylcholine receptors regulate cell adhesion* Life Sci. Mar. 28, 2003;72(18-19):2081-5.

Nguyen, V., et al., *Programmed cell death of keratinocytes culminates in apoptotic secretion of a humectant upon secretagogue action of acetylcholine* J. Cell Sci. Mar. 2001;114(Pt 6):1189-204.

Nicholas, A. et al., *Glutamate-like immunoreactivity in medulla oblongata catecholamine/substance P neurons*, NeuroReport 1990; 1: 235-238.

Palacios, J., et al., *Cholinergic neuropharmacology: an update*, Acta Psychiatr Scand Suppl. 1991;366:27-33.

Pan, C., et al., (2001) *Degeneration of nociceptive nerve terminals in human peripheral neuropathy.*, Neuroreport. 12(4):787-92.

Pearce, L.B., *Pharmacologic Characterization of Botulinum Toxin For Basic Science and Medicine*, Toxicon 35(9);1373-1412 at 1393.

Rogers, J., et al., *Injections of botulinum toxin A in foot dystonia*, Neurology Apr. 1993;43(4 Suppl 2).

Sanchez-Prieto, J., et al., *Botulinum Toxin A Blocks Glutamine Exocytosis From Guinea Pig Cerebral Cortical Synaptosomes*, Eur J. Biochem 165;675-681:1897.

Schantz, E.J., et al., *Properties and use of Botulinum toxin and Other Microbial Neurotoxins in Medicine*, Microbiol Rev. 56;80-99:1992.

Senior, M., *Botox and the management of pectoral spasm after subpectoral implant insertion*, Plastic and Recon Surg, Jul. 2000, 224-225.

Sevim, S., et al., *Botulinum toxin-A therapy for palmar and plantar hyperhidrosis*, Acta Neurol Belg Dec. 2002;102(4):167-70.

Singh, *Critical Aspects of Bacterial Protein Toxins*, pp. 63-84 (chapter 4) of Natural Toxins II, edited by B.R. Singh et al., Plenum Press, New York (1976).

Sloop, R. et al., *Reconstituted botulinum toxin type A does not lose potency in humans if it is refrozen or refrigerated before 2 weeks use*, Neurology 48 (Jan. 1997):249-53:1997.

Sneddon, P., et al., *Pharamcological evidence that adenosine triphosphate and noradrenaline are cotransmitters in the guinea-pig vas deferens*. J. Physiol. 1984; 347: 561-580.

Suputtitada, A., *Local botulinum toxin type A injections in the treatment of spastic toes*, Am J Phys Med Rehabil Oct. 2002;81(10):770-5.

Tacks, L., et al., *Idiopathic toe walking: Treatment with botulinum toxin A injection*, Dev Med Child Neurol 2002;44(Suppl 91):6.

Weigand, et al., *Naunyn-Schmiedeberg's Arch. Pharmacol.* 1976; 292, 161-165.

Whitehouse, P., et al., *Nicotinic and muscarinic cholinergic receptors in Alzheimer's disease and related disorders*, J Neural Transm Suppl. 1987;24:175-82.

Wu, T., et al., *Demonstration of human papillomavirus (HPV) genomic amplification and viral-like particles from CaSki cell line SCID mice*, J Virol Methods 1997;65:287-298.

Xu, Z-QD., et al, *Galanin/GMAP- and NPY-like immunoreactivities in locus coeruleus and noradrenergic nerve terminals in the hippocampal formation and cortex with notes on the galanin-R1 and -R2 receptors*, J. Comp. Neurol. 1998; 392: 227-252.

Xu, Z-QD., et al, *Galanin-5 hydroxytryptamine interactions: Electrophysiological, immunohistochemical and in situ hybridization studies on rat dorsal raphe neurons with a note on galanin R1 and R2 receptors*. Neuroscience 1998; 87: 79-94.

Zia, S., et al., *Receptor-mediated inhibition of keratinocyte migration by nicotine involves modulations of calcium influx and intracellular concentration*, J Pharmacol Exp Ther. Jun. 2000;293(3):973-81.

Database WPI, Section Ch, Week 200332, Derwent Publications Ltd., London, GB; AN 2003-334169, XP002358811 & CN 1 383 811 A (LU W); Dec. 11, 2002; abstract.

* cited by examiner

STRETCH MARK TREATMENT

BACKGROUND

The present invention relates to methods for treating stretch marks. In particular the present invention relates to methods for treating stretch marks by administration of a Clostridial neurotoxin, such as a *botulinum* toxin, to a patient.

Stretch Marks

The skin (synonymously the cutis), a protective membrane covering the exterior of body, is comprised of three layers, the epidermis (the outer layer of the skin), the dermis (the middle layer of the skin) and the stratum or deepest layer. Stretch marks (also known as stria atrophica and striae distensae) occur in the dermis. The dermis is an elastic, resilient middle layer which allows skin to retain its shape. When the dermis is stretched over time as in pregnancy or obesity, the skin becomes less elastic and connective fibers in the dermis can break and tear. The result is stretch marks. Stretch marks begin as raised pink, reddish brown or dark brown striations that can then turn a brighter violet or purple. When first formed a stretch mark can be consist of flattened, thin skin with a pink hue and may occasionally be pruritic. Gradually, a stretch mark can enlarge in length and width and become reddish purple in appearance (forming a striae rubra). The surface of a stretch mark can be finely wrinkled. Mature stretch marks can be white, depressed, irregularly shaped bands, with their long axis parallel to the lines of skin tension. They can be several centimeters long and 1-10 mm wide.

As noted, stretch marks can occur in areas of the body where the skin is subjected to a continuous and/or progressive stretching and may be a result of underlying muscle tension. Skin distension resulting in stretch marks can occur on the abdomen and the breasts of pregnant women, on the shoulders of body builders, in adolescents undergoing their growth spurt, and in individuals who are overweight. Skin distension apparently leads to excessive mast cell degranulation with subsequent damage of collagen and elastin. Such damage is evident in stretch marks due to pregnancy, lactation, weight lifting, and other stressful activities, or other activities that may result in tension build up in the dermis.

In the United States it is estimated that about 90% of pregnant women, 70% of adolescent females, and 40% of adolescent males (many of whom participate in sports) have stretch marks. Stretch marks are usually a cosmetic problem; however, if extensive, they may tear and ulcerate when an accident or excessive stretching occurs.

In pregnancy, stretch marks usually affect the abdomen and the breasts. The most common sites for stretch marks on adolescents are the outer aspects of the thighs and the lumbosacral region in boys and the thighs, the buttocks, and the breasts in girls. Considerable variation occurs, and other sites, including the outer aspects of the upper arms, are occasionally affected. Stretch marks induced by prolonged systemic steroid use are usually larger and wider than other phenotypes of stretch marks, and they involve widespread areas, occasionally including the face.

Stretch marks secondary to topical steroid use are usually related to enhanced potency of the steroids when using occlusive plastic wraps. They usually affect the flexures and may become less visible if the offending treatment is withheld early enough.

In linear focal elastosis (elastatic striae), asymptomatic, yellow linear bands arrange themselves horizontally over the lower back. These lesions may resemble striae distensae, but they are palpable rather than depressed and yellow rather than purplish or white.

In the early stages, inflammatory changes may predominate; edema is present in the dermis along with perivascular lymphocyte cuffing. In the later stages, the epidermis becomes thin and flattened with loss of the rete ridges. The dermis has thin, densely packed collagen bundles arranged in a parallel array horizontal to the epidermis at the level of the papillary dermis. Elastic stains show inconvenience breakage and retraction of the elastic fibers in the reticular dermis. The broken elastic fibers curl at the sides of the striae to form a distinctive pattern.

Scanning electron microscopy shows extensive tangles of fine, curled elastic fibers with a random arrangement. This arrangement is in contrast to normal skin, which has thick, elastic fibers with a regular distribution. When viewed by transmission electron microscopy, the ultrastructure of elastic and collagen fibers in striae is similar to that of healthy skin.

Z Stretch marks are caused by tearing in the skin/connective tissue, either by direct trauma or by "stretching" due to enlargement of tissue, such as muscle, underlying the skin and tissue immediately under the skin.

Numerous creams, ointments and other therapies have been used to try and treat stretch marks, but none are very effective. Additionally, topical and systemic pharmaceuticals and/or surgery to excise stretch marks can have unwanted side effects and there can unfortunately be a significant reoccurrence of the stretch mark after surgery, as well as the possibly of infection.

Limited success has been reported using low concentrations (15-20%) of trichloroacetic acid (TCA) and performing repetitive papillary dermis-level chemexfoliation. The peels can be repeated at monthly intervals. Significant improvement in regard to skin texture, firmness, and color can be achieved. Treatment with the 585-nm flashlamp pulsed dye laser at low energy densities was shown to improve the appearance of striae. Multiple treatments at 4- to 6-week intervals are usually required.

Botulinum Toxin

The genus *Clostridium* has more than one hundred and twenty seven species, grouped according to their morphology and functions. The anaerobic, gram positive bacterium *Clostridium botulinum* produces a potent polypeptide neurotoxin, *botulinum* toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The *botulinum* toxin can apparently pass unattenuated through the lining of the gut and attack peripheral motor neurons. Symptoms of *botulinum* toxin intoxication can progress from difficulty walking, swallowing, and speaking to paralysis of the respiratory muscles and death.

Botulinum toxin type A is the most lethal natural biological agent known to man. About 50 picograms of a commercially available *botulinum* toxin type A (purified neurotoxin complex)1 is a LD50 in mice (i.e. 1 unit). One unit of BOTOX® contains about 50 picograms (about 56 attomoles) of *botulinum* toxin type A complex. Interestingly, on a molar basis, *botulinum* toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins*, pages 63-84 (chapter 4) of Natural Toxins II, edited by B. R. Singh et al., Plenum Press, New York (1976) (where the stated LD50 of botulinum toxin type A of 0.3 ng equals 1 U is corrected for the fact that about 0.05 ng of BOTOX® equals 1 unit). One unit (U) of botulinum toxin is defined as the LD50 upon intraperitoneal injection into female Swiss Webster mice weighing 18 to 20 grams each.

Seven generally immunologically distinct botulinum neurotoxins have been characterized, these being respectively botulinum neurotoxin serotypes A, B, C1, D, E, F and G each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate LD50 for botulinum toxin type A. Moyer E et al., *Botulinum Toxin Type B: Experimental and Clinical Experience*, being chapter 6, pages 71-85 of "*Therapy With Botulinum Toxin*", edited by Jankovic, J. et al. (1994), Marcel Dekker, Inc. Botulinum toxin apparently binds with high affinity to cholinergic motor neurons, is translocated into the neuron and blocks the release of acetylcholine. Additional uptake can take place through low affinity receptors, as well as by phagocytosis and pinocytosis.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of botulinum toxin and for tetanus toxin. The carboxyl end segment of the H chain, HC, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, HN, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of botulinum toxin activity appears to involve reduction of the disulfide bond joining the heavy chain, H chain, and the light chain, L chain. The entire toxic activity of botulinum and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Botulinum toxin serotype A and E cleave SNAP-25. Botulinum toxin serotype C1 was originally thought to cleave syntaxin, but was found to cleave syntaxin and SNAP-25. Each of the botulinum toxins specifically cleaves a different bond, except botulinum toxin type B (and tetanus toxin) which cleave the same bond. Each of these cleavages block the process of vesicle-membrane docking, thereby preventing exocytosis of vesicle content.

Botulinum toxins have been used in clinical settings for the treatment of neuromuscular disorders characterized by hyperactive skeletal muscles (i.e. motor disorders). In 1989, a botulinum toxin type A complex has been approved by the U.S. Food and Drug Administration for the treatment of blepharospasm, strabismus and hemifacial spasm. Subsequently, a botulinum toxin type A was also approved by the FDA for the treatment of cervical dystonia and for the treatment of glabellar lines, and a botulinum toxin type B was approved for the treatment of cervical dystonia. Non-type A botulinum toxin serotypes apparently have a lower potency and/or a shorter duration of activity as compared to botulinum toxin type A. Clinical effects of peripheral intramuscular botulinum toxin type A are usually seen within one week of injection. The typical duration of symptomatic relief from a single intramuscular injection of botulinum toxin type A averages about three months, although significantly longer periods of therapeutic activity have been reported.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type C1 has been shown to cleave both syntaxin and SNAP-25. These differences in mechanism of action may affect the relative potency and/or duration of action of the various botulinum toxin serotypes. Apparently, a substrate for a botulinum toxin can be found in a variety of different cell types. See e.g. *Biochem J* 1; 339 (pt 1):159-65:1999, and *Mov Disord*, 10(3):376:1995 (pancreatic islet B cells contains at least SNAP-25 and synaptobrevin).

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and C1 is apparently produced as only a 700 kD or 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

In vitro studies have indicated that botulinum toxin inhibits potassium cation induced release of both acetylcholine and norepinephrine from primary cell cultures of brainstem tissue. Additionally, it has been reported that *botulinum* toxin inhibits the evoked release of both glycine and glutamate in primary cultures of spinal cord neurons and that in brain synaptosome preparations *botulinum* toxin inhibits the release of each of the neurotransmitters acetylcholine, dopamine, norepinephrine (Habermann E., et al., *Tetanus Toxin and Botulinum A and C Neurotoxins Inhibit Noradrenaline Release From Cultured Mouse Brain*, J Neurochem 51(2); 522-527:1988) CGRP, substance P and glutamate (Sanchez-Prieto, J., et al., *Botulinum Toxin A Blocks Glutamate Exocytosis From Guinea Pig Cerebral Cortical Synaptosomes*, Eur J. Biochem 165; 675-681:1897. Thus, when adequate concentrations are used, stimulus-evoked release of most neurotransmitters is blocked by *botulinum* toxin. See e.g. Pearce, L. B., *Pharmacologic Characterization of Botulinum Toxin For Basic Science and Medicine*, Toxicon 35(9); 1373-1412 at 1393; Bigalke H., et al., *Botulinum A Neurotoxin Inhibits Non-Cholinergic Synaptic Transmission in Mouse Spinal Cord Neurons in Culture*, Brain Research 360; 318-324:1985; Habermann E., *Inhibition by Tetanus and Botulinum A Toxin of the release of [3H]Noradrenaline and [3H]GABA From Rat Brain Homogenate*, Experientia 44; 224-226:1988, Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316; 244-251:1981, and; Jankovic J. et al., *Therapy With Botulinum Toxin*, Marcel Dekker, Inc., (1994), page 5.

Botulinum toxin type A can be obtained by establishing and growing cultures of *Clostridium botulinum* in a fermenter and then harvesting and purifying the fermented mixture in accordance with known procedures. All the *botulinum* toxin serotypes are initially synthesized as inactive single chain proteins which must be cleaved or nicked by proteases to become neuroactive. The bacterial strains that make *botulinum* toxin serotypes A and G possess endogenous proteases and serotypes A and G can therefore be recovered from bacterial cultures in predominantly their active form. In contrast, *botulinum* toxin serotypes C1, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the *botulinum* toxin type B serotype only cleave a portion of the toxin produced. The exact proportion of nicked to unnicked molecules depends on the length of incubation and the temperature of the culture. Therefore, a certain percentage of any preparation of, for example, the *botulinum* toxin type B toxin is likely to be inactive, possibly accounting for the known significantly lower potency of *botulinum* toxin type B as compared to *botulinum* toxin type A. The presence of inactive *botulinum* toxin molecules in a clinical preparation will contribute to the overall protein load of the preparation, which has been linked to increased antigenicity, without contributing to its clinical efficacy. Additionally, it is known that *botulinum* toxin type B has, upon intramuscular injection, a shorter duration of activity and is also less potent than *botulinum* toxin type A at the same dose level.

High quality crystalline *botulinum* toxin type A can be produced from the Hall A strain of *Clostridium botulinum* with characteristics of $\geq 3\times 10^7$ U/mg, an A260/A278 of less than 0.60 and a distinct pattern of banding on gel electrophoresis. The known Shantz process can be used to obtain crystalline *botulinum* toxin type A, as set forth in Shantz, E. J., et al, *Properties and use of Botulinum toxin and Other Microbial Neurotoxins in Medicine*, Microbiol Rev. 56; 80-99: 1992. Generally, the *botulinum* toxin type A complex can be isolated and purified from an anaerobic fermentation by cultivating *Clostridium botulinum* type A in a suitable medium. The known process can also be used, upon separation out of the non-toxin proteins, to obtain pure *botulinum* toxins, such as for example: purified *botulinum* toxin type A with an approximately 150 kD molecular weight with a specific potency of $1-2\times 10^8$ LD50 U/mg or greater; purified *botulinum* toxin type B with an approximately 156 kD molecular weight with a specific potency of $1-2\times 10^8$ LD50 U/mg or greater, and; purified *botulinum* toxin type F with an approximately 155 kD molecular weight with a specific potency of $1-2\times 10^7$ LD50 U/mg or greater.

Botulinum toxins and/or *botulinum* toxin complexes can be obtained from List Biological Laboratories, Inc., Campbell, Calif.; the Centre for Applied Microbiology and Research, Porton Down, U.K.; Wako (Osaka, Japan), Metabiologics (Madison, Wis.) as well as from Sigma Chemicals of St Louis, Mo. Pure *botulinum* toxin can also be used to prepare a pharmaceutical composition.

As with enzymes generally, the biological activities of the *botulinum* toxins (which are intracellular peptidases) is dependant, at least in part, upon their three dimensional conformation. Thus, *botulinum* toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can stabilized with a stabilizing agent such as albumin and gelatin.

A commercially available *botulinum* toxin containing pharmaceutical composition is sold under the trademark BOTOX® (available from Allergan, Inc., of Irvine, Calif.). BOTOX®G) consists of a purified *botulinum* toxin type A complex, albumin and sodium chloride packaged in sterile, vacuum-dried form. The *botulinum* toxin type A is made from a culture of the Hall strain of *Clostridium botulinum* grown in a medium containing N-Z amine and yeast extract. The *botulinum* toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5° C. BOTOX® can be reconstituted with sterile, non-preserved saline prior to intramuscular injection. Each vial of BOTOX® contains about 100 units (U) of *Clostridium botulinum* toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative; (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about 2° C. to about 8° C. Reconstituted, refrigerated BOTOX® has been reported to retain its potency for at least about two weeks. *Neurology*, 48:249-53:1997.

It has been reported that *botulinum* toxin type A has been used in clinical settings as follows:
(1) about 75-125 units of BOTOX® per intramuscular injection (multiple muscles) to treat cervical dystonia;
(2) 5-10 units of BOTOX® per intramuscular injection to treat glabellar lines (brow furrows) (5 units injected intramuscularly into the procerus muscle and 10 units injected intramuscularly into each corrugator supercilii muscle);
(3) about 30-80 units of BOTOX® to treat constipation by intrasphincter injection of the puborectalis muscle;
(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.
(5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired).
(6) to treat upper limb spasticity following stroke by intramuscular injections of BOTOX® into five different upper limb flexor muscles, as follows:
(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.
(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

It is known that *botulinum* toxin type A can have an efficacy for up to 12 months (*European J. Neurology* 6 (Supp 4): S111-S1150:1999), and in some circumstances for as long as 27 months, when used to treat glands, such as in the treatment of hyperhydrosis. See e.g. Bushara K., *Botulinum toxin and rhinorrhea*, Otolaryngol Head Neck Surg 1996; 114(3):507, and *The Laryngoscope* 109:1344-1346:1999. However, the usual duration of an intramuscular injection of Botox® is typically about 3 to 4 months.

The success of *botulinum* toxin type A to treat a variety of clinical conditions has led to interest in other *botulinum* toxin serotypes. Two commercially available *botulinum* type A preparations for use in humans are BOTOX®D available from Allergan, Inc., of Irvine, Calif., and Dysport® available from Beaufour Ipsen, Porton Down, England. A Botulinum toxin type B preparation (MyoBloc®) is available from Elan Pharmaceuticals of San Francisco, Calif.

In addition to having pharmacologic actions at the peripheral location, *botulinum* toxins may also have inhibitory effects in the central nervous system. Work by Weigand et al, *Nauny-Schmiedeberg's Arch. Pharmacol.* 1976; 292,161-165, and Habermann, *Nauny-Schmiedeberg's Arch. Pharmacol.* 1974; 281, 47-56 showed that *botulinum* toxin is able to ascend to the spinal area by retrograde transport. As such, a *botulinum* toxin injected at a peripheral location, for example intramuscularly, may be retrograde transported to the spinal cord.

A *botulinum* toxin has also been proposed for or has been used to treat skin bone and tendon wounds (U.S. Pat. No. 6,447,787); intrathecal pain (see e.g. U.S. Pat. No. 6,113, 915); various autonomic nerve disorders, including sweat gland disorders (see e.g. U.S. Pat. No. 5,766,605 and Goldman (2000), Aesthetic Plastic Surgery July-August 24(4): 280-282); tension headache (U.S. Pat. No. 6,458,365); migraine headache pain (U.S. Pat. No. 5,714,468); post-operative pain and visceral pain (U.S. Pat. No. 6,464,986); hair growth and hair retention (U.S. Pat. No. 6,299,893); psoriasis and dermatitis (U.S. Pat. No. 5,670,484); injured muscles (U.S. Pat. No. 6,423,319); various cancers (see e.g. U.S. Pat. Nos. 6,139,845 and 6,063,768), smooth muscle disorders (U.S. Pat. No. 5,437,291); nerve entrapment syndromes (U.S. patent application 2003 0224019); acne (WO 03/011333); neurogenic inflammation (U.S. Pat. No. 6,063,768); otic disorders (see e.g. U.S. Pat. No. 6,265,379); pancreatic disorders (see e.g. U.S. Pat. Nos. 6,143,306 and 6,261,572); prostate disorders, including prostatic hyperplasia, prostate cancer and urinary incontinence (see e.g. U.S. Pat. Nos. 6,365,164 and 6,667,041 and Doggweiler R., et al *Botulinum toxin type A causes diffuse and highly selective atrophy of rat prostate*, Neurourol Urodyn 1998; 17(4):363); fibromyalgia (U.S. Pat. No. 6,623,742); piriformis muscle syndrome (see e.g. Childers et al. (2002), American Journal of Physical Medicine & Rehabilitation, 81:751-759); and various skin disorders (see U.S. patent applications Ser. Nos. 731,973; 814,764, and; 817,036).

U.S. Pat. No. 5,989,545 discloses that a modified clostridial neurotoxin or fragment thereof, preferably a *botulinum* toxin, chemically conjugated or recombinantly fused to a particular targeting moiety can be used to treat pain by administration of the agent to the spinal cord. Additionally it has been disclosed that targeted *botulinum* toxins (i.e. with a non-native binding moiety) can be used to treat various conditions (see e.g. WO 96/33273; WO 99/17806; WO 98/07864; WO 00/57897; WO 01/21213; WO 00/10598.

A *botulinum* toxin has been injected into the pectoral muscle to control pectoral spasm. See e.g. Senior M., *Botox and the management of pectoral spasm after subpectoral implant insertion*, Plastic and Recon Surg, July 2000, 224-225. Controlled release toxin implants are known (see e.g. U.S. Pat. Nos. 6,306,423 and 6,312,708) as is transdermal *botulinum* toxin administration (U.S. patent application Ser. No. 10/194,805).

Both liquid stable formulations and pure *botulinum* toxin formulations have been disclosed (see e.g. WO 00/15245 and WO 74703) as well as topical application of a *botulinum* toxin (see e.g. DE 198 52 981).

It is known that a *botulinum* toxin can be used to: weaken the chewing or biting muscle of the mouth so that self inflicted wounds and resulting ulcers can heal (Payne M., et al, *Botulinum toxin as a novel treatment for self mutilation in Lesch-Nyhan syndrome*, Ann Neurol 2002 Sep; 52(3 Supp 1):S157); permit healing of benign cystic lesions or tumors (Blugerman G., et al., *Multiple eccrine hidrocystomas*: A new therapeutic option with *botulinum* toxin, Dermatol Surg 2003 May; 29(5):557-9); treat anal fissure (Jost W., Ten years' experience with *botulinum* toxin in anal fissure, Int J Colorectal Dis 2002 September; 17(5):298-302, and; treat certain types of atopic dermatitis (Heckmann M., et al., *Botulinum toxin type*

*A injection in the treatment of lichen simplex: An open pilot study*, J Am Acad Dermatol 2002 April; 46(4):617-9).

Additionally, a *botulinum* toxin may have an effect to reduce induced inflammatory pain in a rat formalin model. Aoki K., et al, *Mechanisms of the antinociceptive effect of subcutaneous Botox: Inhibition of peripheral and central nociceptive processing*, Cephalalgia 2003 September; 23(7): 649. Furthermore, it has been reported that *botulinum* toxin nerve blockage can cause a reduction of epidermal thickness. Li Y, et al., *Sensory and motor denervation influences epidermal thickness in rat foot glabrous skin*, Exp Neurol 1997; 147:452-462 (see page 459). Finally, it is known to administer a *botulinum* toxin to the foot to treat excessive foot sweating (Katsambas A., et al., *Cutaneous diseases of the foot: Unapproved treatments*, Clin Dermatol 2002 November-December; 20(6):689-699; Sevim, S., et al., *Botulinum toxin-A therapy for palmar and plantar hyperhidrosis*, Acta Neurol Belg 2002 December; 102(4):167-70), spastic toes (Suputtitada, A., Local *botulinum* toxin type A injections in the treatment of spastic toes, Am J Phys Med Rehabil 2002 October; 81(10):770-5), idiopathic toe walking (Tacks, L., et al., Idiopathic toe walking: Treatment with *botulinum* toxin A injection, Dev Med Child Neurol 2002; 44(Suppl 91):6), and foot dystonia (Rogers J., et al., Injections of *botulinum* toxin A in foot dystonia, Neurology 1993 April; 43(4 Suppl 2)).

Tetanus toxin, as wells as derivatives (i.e. with a non-native targeting moiety), fragments, hybrids and chimeras thereof can also have therapeutic utility. The tetanus toxin bears many similarities to the *botulinum* toxins. Thus, both the tetanus toxin and the *botulinum* toxins are polypeptides made by closely related species of *Clostridium* (*Clostridium tetani* and *Clostridium botulinum*, respectively). Additionally, both the tetanus toxin and the *botulinum* toxins are dichain proteins composed of a light chain (molecular weight about 50 kD) covalently bound by a single disulfide bond to a heavy chain (molecular weight about 100 kD). Hence, the molecular weight of tetanus toxin and of each of the seven *botulinum* toxins (non-complexed) is about 150 kD. Furthermore, for both the tetanus toxin and the *botulinum* toxins, the light chain bears the domain which exhibits intracellular biological (protease) activity, while the heavy chain comprises the receptor binding (immunogenic) and cell membrane translocational domains.

Further, both the tetanus toxin and the *botulinum* toxins exhibit a high, specific affinity for gangliocide receptors on the surface of presynaptic cholinergic neurons. Receptor mediated endocytosis of tetanus toxin by peripheral cholinergic neurons results in retrograde axonal transport, blocking of the release of inhibitory neurotransmitters from central synapses and a spastic paralysis. Contrarily, receptor mediated endocytosis of *botulinum* toxin by peripheral cholinergic neurons results in little if any retrograde transport, inhibition of acetylcholine exocytosis from the intoxicated peripheral motor neurons and a flaccid paralysis.

Finally, the tetanus toxin and the *botulinum* toxins resemble each other in both biosynthesis and molecular architecture. Thus, there is an overall 34% identity between the protein sequences of tetanus toxin and *botulinum* toxin type A, and a sequence identity as high as 62% for some functional domains. Binz T. et al., *The Complete Sequence of Botulinum Neurotoxin Type A and Comparison with Other Clostridial Neurotoxins*, J Biological Chemistry 265(16); 9153-9158: 1990.

Acetylcholine

Typically only a single type of small molecule neurotransmitter is released by each type of neuron in the mammalian nervous system, although there is evidence which suggests that several neuromodulators can be released by the same neuron. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the bag 1 fibers of the muscle spindle fiber, by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

What is needed therefore is a therapeutically effective method for treating a stretch mark.

SUMMARY

The present invention meets this need and provides methods for effectively treating a stretch mark by local administration of a Clostridial neurotoxin.

A method within the scope of the present invention for treating a stretch mark can have the step of local administration of a Clostridial neurotoxin to a location of a stretch mark of a patient, such as to the abdomen, breast or back of a patient. By local administration it is meant that the Clostridial neurotoxin is administered, as by injection, directly to, in, or to the vicinity of, a region of a stretch mark. The neurotoxin can be locally administered in an amount of between about $10^{-3}$ units/kg of patient weight and about 35 units/kg of patient weight. Preferably, the neurotoxin is locally administered in an amount of between about $10^{-2}$ U/kg and about 25 U/kg of patient weight. More preferably, the neurotoxin is administered in an amount of between about $10^{-1}$ U/kg and about 15 U/kg. In a particularly preferred method within the scope of the present invention, the neurotoxin is locally administered in an amount of between about 1 U/kg and about 10 U/kg. In a clinical setting it can be advantageous to inject from 1 U to 3000 U of a neurotoxin, such as *botulinum* toxin type A or B, to a stretch mark location by topical application or by intradermal administration, to effectively treat the stretch mark.

Without wishing to be bound by therapy a mechanism can be proposed for the efficacy of the present invention. It is known that a *botulinum* toxin can be effective to relax muscles and to promote cosmetic healing of skin surface scars. Additionally, a *botulinum* toxin may inhibit release of other mediators such as cGRP (calcitonin gene-related peptide) which can have an effect on mast cell degranulation. There is evidence that the G protein-coupled receptor cGRP-R is expressed in skin cells. cGRP is a potent vasodilator of small and large vessels, at least partly through direct activation of arteriolar smooth muscle cell receptors. cGRP also increases vascular permeability, producing dermal edema through indirect activation of mast cells or through stimulation of nitric oxide (NO) production by endothelial cells with consequent vasodilatation.

Thus, it can be hypothesized that a *botulinum* toxin can by relaxing muscle tissue surrounding a stretch mark reduce tension in the dermis thereby permitting the healing of a stretch mark and preventing the formation of new stretch marks. Additionally, a *botulinum* toxin may treat stretch marks by inhibiting mast cell degranulation as mast cell degranulation is believed to contribute to the formation of stretch marks.

A suitable neurotoxin for use in the practice of the present invention can be made by a Clostridial bacterium, such as *Clostridium botulinum*, *Clostridium butyricum* or *Clostridium beratti*. The neurotoxin use can be a modified neurotoxin that is a neurotoxin has had at least one of its amino acids deleted, modified or replaced, as compared to a native neurotoxin. Additionally, the neurotoxin can be recombinantly made produced neurotoxin or a derivative or fragment of a recombinant made neurotoxin. The neurotoxin can be a *botulinum* toxin, such as one of the *botulinum* toxin serotypes A, B, $C_1$, D, E, F or G. A preferred *botulinum* toxin to use in the practice of the present invention is *botulinum* toxin type A.

A method according to my invention can be carried out by administration of a Clostridial toxin to a patient with, or who is predisposed to, stretch mark. The Clostridial toxin used is preferably a *botulinum* toxin (as either a complex or as a pure [i.e. about 150 kDa molecule], such as a *botulinum* toxin A, B, C, D, E, F or G. Administration of the Clostridial toxin can be by a transdermal route (i.e. by application of a Clostridial toxin in a cream, patch or lotion vehicle), subdermal route (i.e. subcutaneous or intramuscular) or intradermal route of administration.

The dose of a Clostridial toxin used according to the present invention is less than the amount of toxin that would be used to paralyze a muscle, since the intent of a method according to the present invention is not to paralyze a muscle but to treat a stretch mark.

The following definitions apply herein:

"About" means approximately or nearly and in the context of a numerical value or range set forth herein means ±10% of the numerical value or range recited or claimed.

"Alleviating" means a reduction in the visual prominence of a stretch mark. Thus, alleviating includes some reduction, significant reduction, near total reduction, and total reduction of a stretch mark symptom. An alleviating effect may not appear clinically for between 1 to 7 days after administration of a Clostridial neurotoxin to a patient.

"Botulinum toxin" means a *botulinum* neurotoxin as either pure toxin (i.e. about 150 kDa weight molecule) or as a complex (i.e. about 300 to about 900 kDa weight complex comprising a neurotoxin molecule and one or more associated non-toxic molecules), and excludes *botulinum* toxins which are not neurotoxins such as the cytotoxic *botulinum* toxins C2 and C3, but includes recombinantly made, hybrid, modified, and chimeric *botulinum* toxins.

"Local administration" or "locally administering" means administration (i.e. by a subcutaneous, intramuscular, subdermal or transdermal route) of a pharmaceutical agent to or to the vicinity of a dermal or subdermal location of a patient.

"Treating" means to alleviate (or to eliminate) at least one symptom of a stretch mark, either temporarily or permanently.

The Clostridial neurotoxin is administered in a therapeutically effective amount to alleviate a symptom of a stretch mark. A suitable Clostridial neurotoxin may be a neurotoxin made by a bacterium, for example, the neurotoxin may be made from a *Clostridium botulinum, Clostridium butyricum,* or *Clostridium beratti*. In certain embodiments of the invention, the stretch mark can be treated by applying to (topical) or into (intra or transdermal) the skin of a patient a *botulinum* toxin. The *botulinum* toxin can be a *botulinum* toxin type A, type B, type C1, type D, type E, type F, or type G. The stretch mark alleviating effects of the *botulinum* toxin may persist for between about 2 weeks (i.e. upon administration of a short acting *botulinum* toxin, such as a *botulinum* toxin type E) and 5 years (i.e. upon implantation of a controlled release *botulinum* toxin implant). The *botulinum* neurotoxin can be a recombinantly made *botulinum* neurotoxins, such as *botulinum* toxins produced by an *E. coli* bacterium. In addition or alternatively, the *botulinum* neurotoxin can be a modified neurotoxin, that is a *botulinum* neurotoxin which has at least one of its amino acids deleted, modified or replaced, as compared to a native or the modified *botulinum* neurotoxin can be a recombinant produced *botulinum* neurotoxin or a derivative or fragment thereof.

A method for treating a stretch mark according to the present invention can comprise the step of local administration of a *botulinum* toxin to a patient with a stretch mark to thereby alleviate the stretch mark. The *botulinum* toxin can be selected from the group consisting of *botulinum* toxin types A, B, C, D, E, F and G. Botulinum toxin type A is a preferred *botulinum* toxin.

A detailed embodiment of my invention can comprise a method for treating a stretch mark by local administration to a patient with a stretch mark of between about 1 unit and about 3,000 units of a *botulinum* toxin (for example between about 1-50 units of a *botulinum* toxin type A or between about 50 to 3,000 units of a *botulinum* toxin type B), thereby alleviating the stretch mark for between about two weeks and about 5 years.

My invention also encompasses a method for treating stretch mark by locally administering a *botulinum* toxin (such as a *botulinum* toxin type A, B, C, D, E, F or G, in an amount of from 1 unit to 3,000 units per treatment session) to a patient predisposed to experience stretch mark, thereby preventing the patient from experiencing a stretch mark. A patient predisposed to stretch mark is a human who has experienced stretch mark at least once within the last twelve months. The local administration can be carried out by subcutaneous or by topical administration of the *botulinum* toxin a location on or within the skin of the patient where a stretch mark is located. The stretch mark can be reduced in size by from about 20% to 100%.

DESCRIPTION

The present invention is based upon the discovery that a stretch mark can be treated by local administration of a therapeutically effective amount of a Clostridial neurotoxin, such as a *botulinum* neurotoxin. The *botulinum* neurotoxin (such as a *botulinum* neurotoxin serotype A, B, $C_1$ D, E, F or G) can be injected into or topically applied onto or in the vicinity of a stretch mark of a patient. Alternately, the *botulinum* toxin can be administered to an intradermal or subdermal neuron to thereby downregulate, inhibit or suppress a neuronally mediated or influenced stretch mark.

Without wishing to be bound by theory a physiological mechanism can be proposed for the efficacy of my invention as disclosed herein for the treatment of a stretch mark using a Clostridial neurotoxin. Essentially, it is hypothesized that use of a *botulinum* toxin can inhibit release of acetylcholine and/ or of another neurotransmitter or neuropeptide by one or more dermal nerves or structures which innervate or which influence a stretch mark, to thereby permit effective treatment of a stretch mark. Alternately, the administered Clostridial neurotoxin may have a direct effect upon the stretch mark. By effective treatment it is meant that the stretch mark becomes less painful, less inflamed and/or regresses (i.e. becomes smaller in size [i.e. thinner] or disappears altogether).

With regard to a proposed physiological mechanism for use of a Clostridial neurotoxin to treat a stretch mark as set forth herein, it is known that human keratinocytes can respond to acetylcholine. It is believed that acetylcholine is released by keratinocytes to function as a local hormone in the epidermis. Grando S. et al., *Human keratinocytes synthesize, secrete and degrade acetylcholine*, J Invest Dermatol. 1993 July; 101(1):32-6. Human epidermal keratinocytes possess cholinergic enzymes, which synthesize and degrade acetylcholine, and express both nicotinic and muscarinic classes of cholinergic receptors on their cell surfaces. These epidermal keratinocyte cell surface receptors bind acetylcholine and initiate various cellular responses. Significantly, the presence in keratinocytes of a functional cholinergic system suggests a role for acetylcholine in most, if not all, aspects of keratinocyte function. Acetylcholine employs calcium as a mediator for its effects on keratinocytes. In turn, changes in calcium concentration can affect expression and function of keratinocyte cholinergic enzymes and cholinergic receptors. At different stages of their differentiation, keratinocytes demonstrate unique combinations of cholinergic enzymes and cholinergic receptor types. Grando S., *Biological functions of keratinocyte cholinergic receptors*, J Investig Dermatol Symp Proc. 1997 August; 2(1):41-8.

Importantly, skin innervation exerts influence on the proliferation of keratinocytes and the thickness of the epidermis. Huang et al., *Influence of cutaneous nerves on keratinocyte proliferation and epidermal thickness in mice*. Neuroscience. 1999; 94(3):965-73. Several lines of evidence suggest that nerves which terminate in the skin have profound influences on their target, the epidermis. See e.g. Grando S., *Biological functions of keratinocyte cholinergic receptors*, J Investig Dermatol Symp Proc. 1997 August; 2(1):41-8; Grando S., et al., *Activation of keratinocyte nicotinic cholinergic receptors stimulates calcium influx and enhances cell differentiation*. Invest Dermatol. 1996 September; 107(3):412-8; Ndoye A., et al., *Identification and mapping of keratinocyte muscarinic acetylcholine receptor subtypes in human epidermis*, J Invest Dermatol. 1998 September; 111(3):410-6; Palacios J., et al., *Cholinergic neuropharmacology: an update*, Acta Psychiatr Scand Suppl. 1991; 366:27-33; Whitehouse P., et al., *Nicotinic and muscarinic cholinergic receptors in Alzheimer's disease and related disorders*, J Neural Transm Suppl. 1987; 24:175-82; Arredondo J., et al., *Central role of alpha7 nicotinic receptor in differentiation of the stratified squamous epithelium*, J. Cell Biol. 2002 Oct. 28; 159(2):325-36; Andreadis S., et al., *Keratinocyte growth factor induces hyperproliferation and delays differentiation in a skin equivalent model system*, FASEB J. 2001 April; 15(6):898-906; Krnjevic K., *Central cholinergic mechanisms and function*. Prog Brain Res. 1993; 98:285-92; *Epidermal expression of the full-length extracellular calcium-sensing receptor is required for normal keratinocyte differentiation*, J Cell Physiol. 2002 July; 192(1):45-54; Grando S., et al., *Human keratinocytes synthesize, secrete, and degrade acetylcholine* J Invest Dermatol. 1993 July; 101 (1):32-6; Zia S., et al., *Receptor-mediated inhibition of keratinocyte migration by nicotine involves modulations of calcium influx and intracellular concentration*, J Pharmacol Exp Ther. 2000 June; 293 (3):973-81; Nguyen V., et al., *Keratinocyte acetylcholine receptors regulate cell adhesion* Life Sci. 2003 Mar. 28; 72(18-19):2081-5; Nguyen V., et al., *Programmed cell death of keratinocytes culminates in apoptotic secretion of a humectant upon secretagogue action of acetylcholine* J Cell Sci. 2001 March; 114(Pt 6):1189-204; Grando S., et al., *Keratinocyte muscarinic acetylcholine receptors: immunolocalization and partial characterization*, J Invest Dermatol. 1995 January; 104(1):95-100; Lin Y., et al., (2001) *Cutaneous nerve terminal degeneration in painful mononeuropathy*, Experimental Neurology. 170(2):290-6; Pan C., et al., (2001) *Degeneration of nociceptive nerve terminals in human peripheral neuropathy*, Neuroreport. 12(4):787-92; Hsiung-F., et al., (2001) *Quantitative pathology of cutaneous nerve terminal degeneration in the human skin*, Acta Neuropathologica 102:455-461; Ko M., et al., *Cutaneous nerve degeneration induced by acrylamide in mice*, Neuroscience Letters. (2000)293(3):195-8; Lin Y., et al., *Quantitative sensory test-* ing: normative values and its application in diabetic neuropathy, Acta Neurol Taiwan 1998; 7:176-184; T. Huang, et al., *Influence of cutaneous nerves on keratinocyte proliferation and epidermal thickness in mice*, Neuroscience 94:965-973, 1999; Hsieh S., et al., *Pathology of nerve terminal degeneration in the skin*, Journal of Neuropathology & Experimental Neurology. 2000; 59(4):297-307; Huang I. et al., *Influence of cutaneous nerves on keratinocyte proliferation and epidermal thickness in mice*, Neuroscience. 1999; 94(3):965-73; Hsieh S., et al., *Modulation of keratinocyte proliferation by skin innervation*. Journal of Investigative Dermatology, 1999; 113(4):579-86; Chen W., et al., *Trophic interactions between sensory nerves and their targets*, Journal of Biomedical Science. 1999; 6(2):79-85; Chiang H-Y, et al., *Regional difference in epidermal thinning after skin denervation*, Exp Neurol 1998; 154(1):137-45; Hsieh S., et al., *Skin innervation and its influence on the epidermis*, J Biomed Sci 1997; 4:264-268; Lee M., et al., *Clinical and electrophysiological characteristics of inflammatory demyelinating neuropathies*, Acta Neurol Taiwan 1997; 6:283-288; Wu T., et al., *Demonstration of human papillomavirus (HPV) genomic amplification and viral-like particles from CaSki cell line in SCID mice*, J Virol Methods 1997; 65:287-298; Hsieh S., et al., *Epidermal denervation and its effects on keratinocytes and Langerhans cells*, J Neurocytol 1996; 25:513-524; McCarthy B., et al., *Cutaneous innervation in sensory neuropathies: evaluation by skin biopsy*, Neurol 1995; 45:1848-1855; Griffin J., et al., *Axonal degeneration and disorders of the axonal cytoskeleton*. In: Waxman S., et al., *The Axon*. New York: Oxford University Press, 1995:375-390.

Thus, it can be postulated that a *botulinum* toxin can be used to induce denervation and thereby can treat a stretch mark—by preventing (i.e. downregulating) the release of various neuropeptides released by nerves which innervate the skin. Among these neuropeptides are the tachykinins, substance P and neurokinin A, calcitonin gene-related peptide (CGRP), vasoactive intestinal peptide (VIP) and somatostatin, all of which have been reported to modulate skin cell functions such as cell proliferation. As set forth previously, release of most neurotransmitters and related neuropeptides can be blocked by *botulinum* toxin. See e.g. Hokfelt T., *Neuropeptides in perspective: The last ten years*, Neuron 1991; 7: 867-879; Xu Z-QD et al, *Galanin/GMAP-and NPY-like immunoreactivities in locus coeruleus and noradrenergic nerve terminals in the hippocampal formation and cortex with notes on the galanin-R1 and -R2 receptors*, J. Comp. Neurol. 1998; 392: 227-252; Xu Z-QD et al, *Galanin-5-hydroxytryptamine interactions: Electrophysiological, immunohistochemical and in situ hybridization studies on rat dorsal raphe neurons with a note on galanin R1 and R2 receptors*. Neuroscience 1998; 87: 79-94; Johnson M., *Synaptic glutamate release by postnatal rat serotonergic neurons in microculture*, Neuron 1994; 12: 433-442; Sneddon P., et al., *Pharamcological evidence that adenosine triphosphate and noradrenaline are cotransmitters in the guinea-pig vas deferens*. J. Physiol. 1984; 347: 561-580; Kaneko T., et al., *Immunohistochemical demonstration of glutaminase in catecholaminergic and serotonergic neurons of rat brain*, Brain Res. 1990; 507: 141-154; Kasakov L., et al., *Direct evidence for concomitant release of noradrenaline, adenosine 5'-triphosphate and neuropeptide Y from sympathetic nerve supplying the guinea-pig vas deferens*. J. Auton. Nerv. Syst. 1988; 22: 75-82; Nicholas A. et al., *Glutamate-like immunoreactivity in medulla oblongata catecholamine/substance P neurons*, NeuroReport 1990; 1: 235-238; Nicholas A. et al., Kupfermann I., *Functional studies of cotransmission*. Physiol. Rev. 1991; 71: 683-732.48: 545-59; Lundberg J., *Pharmacology of cotransmission in the autonomic nervous system: Integrative aspects on amines, neuropeptides, adenosine triphosphate, amino acids and nitric oxide*, Pharmacol. Rev. 1996; 48: 113-178; Hsieh S., et al., *Skin Innervation and Its Effects on the Epidermis*, J Biomed Sci. 1997; 4(5):264-268; Legat F., et al., *Repeated subinflammatory ultraviolet B irradiation increases substance P and calcitonin gene-related peptide content and augments mustard oil-induced neurogenic inflammation in the skin of rats*, Neurosci Lett. 2002 Sep. 6; 329(3):309-13; White S., et al., Asahina A., et al., *Specific induction of cAMP in Langerhans cells by calcitonin gene-related peptide: relevance to functional effects*, Proc Natl Acad Sci USA. 1995 Aug. 29; 92(18):8323-7; Inaba N., et al., *Capsaicin-induced calcitonin gene-related peptide release from isolated rat stomach measured with a new chemiluminescent enzyme immunoassay*, Jpn J. Pharmacol. 1996 November; 72(3):223-9; Hosoi J., et al., *Regulation of Langerhans cell function by nerves containing calcitonin gene-related peptide*, Nature. 1993 May 13; 363(6425):159-63.

FIG. 1 illustrates a mechanism of action of a *botulinum* toxin ("Btx" in FIG. 1). A *botulinum* toxin can inhibit release of cGRP, SP, and glutamate from dermal sensory nerves, and also inhibit direct release of these mediators from skin keratinocyte, endothelial and melanocyte cells. It is known that neuropeptides released by sensory nerves that innervate the skin and contact epidermal and dermal cells can directly modulate functions of keratinocytes, Langerhans cells (LC), mast cells, dermal microvascular endothelial cells and infiltrating immune cells. In FIG. 1 NO is nitrous oxide, cGRP is calcitonin gene-related peptide, Ach is acetylcholine, cGRP-R is the receptor for the cGRP molecule, v-dil means vasodilation and SP is substance P.

Furthermore, it has been demonstrated that denervation of the skin can cause the epidermis to began to degenerate or to become thinner. Hsieh S., et al., *Modulation of keratinocyte proliferation by skin innervation*, J Invest Dermatol. 1999 October; 113(4):579-86; Hsieh S., et al., *Epidermal denervation and its effects on keratinocytes and Langerhans cells*, J Neurocytol. 1996 September; 25(9):513-24.); Chiang, et al., *Regional difference in epidermal thinning after skin denervation*, Exp Neurol 1998 November; 154(1):137-45; Li Y., et al., *Sensory and motor denervation influence epidermal thickness in rat foot glabrous skin*, Exp Neurol. 1997 October; 147(2):452-62 (*botulinum* toxin blockade caused epidermal thickness to be significantly reduced in the central area of the sole of the rat foot).

The amount of the Clostridial toxin administered according to a method within the scope of the disclosed invention can vary according to the particular characteristics of the stretch mark being treated, including its severity and other various patient variables including size, weight, age, and responsiveness to therapy. To guide the practitioner, typically, no less than about 1 unit and no more than about 50 units of a *botulinum* toxin type A (such as BOTOX®) is administered per injection site (i.e. to each stretch mark location injected), per patent treatment session. For a *botulinum* toxin type A such as DYSPORT®, no less than about 2 units and no more about 200 units of the *botulinum* toxin type A are administered per administration or injection site, per patent treatment session. For a *botulinum* toxin type B such as MYOBLOC®, no less than about 40 units and no more about 2500 units of the *botulinum* toxin type B are administered per administer or injection site, per patent treatment session. Less than about 1, 2 or 40 units (of BOTOX®, DYSPORT® and MYOBLOC® respectively) can fail to achieve a desired therapeutic effect, while more than about 50, 200 or 2500 units (of BOTOX®, DYSPORT® and MYOBLOC® respectively) can result in clinically observable and undesired muscle hypotonicity, weakness and/or paralysis.

More preferably: for BOTOX® no less than about 2 units and no more about 20 units of a *botulinum* toxin type A; for DYSPORT® no less than about 4 units and no more than about 100 units, and; for MYOBLOC®, no less than about 80 units and no more than about 1000 units are, respectively, administered per injection site, per patent treatment session.

Most preferably: for BOTOX® no less than about 5 units and no more about 15 units of a *botulinum* toxin type A; for DYSPORT® no less than about 20 units and no more than about 75 units, and; for MYOBLOC®, no less than about 200 units and no more than about 750 units are, respectively, administered per injection site, per patent treatment session. It is important to note that there can be multiple injection sites (i.e. a pattern of injections) for each patient treatment session.

Although examples of routes of administration and dosages are provided, the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., 14th edition, published by McGraw Hill). For example, the route and dosage for administration of a Clostridial neurotoxin according to the present disclosed invention can be selected based upon criteria such as the solubility characteristics of the neurotoxin chosen as well as the intensity and scope of a stretch mark.

The present invention is based on the discovery that local administration of a Clostridial toxin can provide significant and long lasting relief from a stretch mark. A Clostridial toxin used in accordance with the invention disclosed herein can inhibit transmission of chemical or electrical signals between select neuronal groups that are involved in generation of a stretch mark. The Clostridial toxins preferably are not cytotoxic to the cells that are exposed to the Clostridial toxin. The Clostridial toxin can inhibit neurotransmission by reducing or preventing exocytosis of neurotransmitter from the neurons exposed to the Clostridial toxin. Or the applied Clostridial toxin can reduce neurotransmission by inhibiting the generation of action potentials of the neurons exposed to the toxin. The stretch mark alleviation effect provided by the Clostridial toxin can persist for a relatively long period of time, for example, for more than two months, and potentially for several years.

Examples of Clostridial toxins within the scope of the present invention include neurotoxins made by *Clostridium botulinum, Clostridium butyricum* and *Clostridium beratti* species. In addition, the *botulinum* toxins used in the methods of the invention may be a *botulinum* toxin selected from a group of *botulinum* toxin types A, B, C, D, E, F, and G. In one embodiment of the invention, the *botulinum* neurotoxin administered to the patient is *botulinum* toxin type A. Botulinum toxin type A is desirable due to its high potency in humans, ready availability, and known use for the treatment of skeletal and smooth muscle disorders when locally administered by intramuscular injection. The present invention also includes the use of (a) Clostridial neurotoxins obtained or processed by bacterial culturing, toxin extraction, concentration, preservation, freeze drying, and/or reconstitution; and/ or (b) modified or recombinant neurotoxins, that is neurotoxins that have had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made. These neurotoxin variants retain the ability to inhibit neurotransmission between or among neurons, and some of these variants may provide increased durations of inhibitory effects as compared to native neurotoxins, or may provide enhanced binding specificity to the neurons exposed to the neurotoxins. These neurotoxin variants may be selected by screening the variants using conventional assays to identify neurotoxins that have the desired physiological effects of inhibiting neurotransmission.

Botulinum toxins for use according to the present invention can be stored in lyophilized, vacuum dried form in containers under vacuum pressure or as stable liquids. Prior to lyophilization the *botulinum* toxin can be combined with pharmaceutically acceptable excipients, stabilizers and/or carriers, such as albumin. The lyophilized material can be reconstituted with saline or water to create a solution or composition containing the *botulinum* toxin to be administered to the patient.

Although the composition may only contain a single type of neurotoxin, such as *botulinum* toxin type A, as the active ingredient to suppress neurotransmission, other therapeutic compositions may include two or more types of neurotoxins, which may provide enhanced therapeutic treatment of a stretch mark. For example, a composition administered to a patient may include *botulinum* toxin type A and *botulinum* toxin type B. Administering a single composition containing two different neurotoxins can permit the effective concentration of each of the neurotoxins to be lower than if a single neurotoxin is administered to the patient while still achieving the desired therapeutic effects. The composition administered to the patient may also contain other pharmaceutically active ingredients, such as, protein receptor or ion channel modulators, in combination with the neurotoxin or neurotoxins. These modulators may contribute to the reduction in neurotransmission between the various neurons. For example, a composition may contain gamma aminobutyric acid (GABA) type A receptor modulators that enhance the inhibitory effects mediated by the GABAA receptor. The GABAA receptor inhibits neuronal activity by effectively shunting current flow across the cell membrane. GABAA receptor modulators may enhance the inhibitory effects of the GABAA receptor and reduce electrical or chemical signal transmission from the neurons. Examples of GABAA receptor modulators include benzodiazepines, such as diazepam, oxaxepam, lorazepam, prazepam, alprazolam, halazeapam, chordiazepoxide, and chlorazepate. Compositions may also contain glutamate receptor modulators that decrease the excitatory effects mediated by glutamate receptors. Examples of glutamate receptor modulators include agents that inhibit current flux through AMPA, NMDA, and/or kainate types of glutamate receptors. The compositions may also include agents that modulate dopamine receptors, such as antipsychotics, norepinephrine receptors, and/or serotonin receptors. The compositions may also include agents that affect ion flux through voltage gated calcium channels, potassium channels, and/or sodium channels. Thus, the compositions used to treat a stretch mark can include one or more neurotoxins, such as *botulinum* toxins, in addition to ion channel receptor modulators that may reduce neurotransmission.

The neurotoxin may be administered by any suitable method as determined by the attending physician. The methods of administration permit the neurotoxin to be administered locally to a selected target tissue. Methods of administration include injection of a solution or composition containing the neurotoxin, as described above, and include implantation of a controlled release system that controllably releases the neurotoxin to the target tissue. Such controlled release systems reduce the need for repeat injections. Diffusion of biological activity of a *botulinum* toxin within a tissue appears to be a function of dose and can be graduated. Jankovic J., et al *Therapy With Botulinum Toxin*, Marcel Dekker, Inc., (1994), page 150. Thus, diffusion of *botulinum* toxin can be controlled to reduce potentially undesirable side effects that may affect the patient's cognitive abilities. For example, the neurotoxin can be administered so that the neurotoxin primarily effects neural systems believed to be involved in the generation of a stretch mark.

A polyanhydride polymer, Gliadel® (Stolle R & D, Inc., Cincinnati, Ohio) a copolymer of poly-carboxyphenoxypropane and sebacic acid in a ratio of 20:80 has been used to make implants, and has been intracranially implanted to treat malignant gliomas. Polymer and BCNU can be co-dissolved in methylene chloride and spray-dried into microspheres. The microspheres can then be pressed into discs 1.4 cm in diameter and 1.0 mm thick by compression molding, packaged in aluminum foil pouches under nitrogen atmosphere and sterilized by 2.2 megaRads of gamma irradiation. The polymer permits release of carmustine over a 2-3 week period, although it can take more than a year for the polymer to be largely degraded. Brem, H., et al, *Placebo-Controlled Trial of Safety and Efficacy of Intraoperative Controlled Delivery by Biodegradable Polymers of Chemotherapy for Recurrent Gliomas*, Lancet 345; 1008-1012:1995.

Implants useful in practicing the methods disclosed herein may be prepared by mixing a desired amount of a stabilized neurotoxin (such as non-reconstituted BOTOX®) into a solution of a suitable polymer dissolved in methylene chloride. The solution may be prepared at room temperature. The solution can then be transferred to a Petri dish and the methylene chloride evaporated in a vacuum desiccator. Depending upon the implant size desired and hence the amount of incorporated neurotoxin, a suitable amount of the dried neurotoxin incorporating implant is compressed at about 8000 p.s.i. for 5 seconds or at 3000 p.s.i. for 17 seconds in a mold to form implant discs encapsulating the neurotoxin. See e.g. Fung L. K. et al., *Pharmacokinetics of Interstitial Delivery of Carmustine 4-Hydroperoxycyclophosphamide and Paclitaxel From a Biodegradable Polymer Implant in the Monkey Brain*, Cancer Research 58; 672-684:1998.

Local administration of a Clostridial toxin, such as a *botulinum* toxin, can provide a high, local therapeutic level of the toxin. A controlled release polymer capable of long term, local delivery of a Clostridial toxin to a target stretch mark location permits effective dosing of the target tissue. A suitable implant, as set forth in U.S. Pat. No. 6,306,423 entitled "Neurotoxin Implant", allows the direct introduction of a chemotherapeutic agent to a target tissue via a controlled release polymer. The implant polymers used are preferably hydrophobic so as to protect the polymer incorporated neurotoxin from water induced decomposition until the toxin is released into the target tissue environment.

Local administration of a *botulinum* toxin, according to the present invention, by injection or implant to a target tissue provides a superior alternative to systemic administration of pharmaceuticals to patients to alleviate a stretch mark.

The amount of a Clostridial toxin selected for local administration to a target tissue according to the present disclosed invention can be varied based upon criteria such as the severity of the stretch mark being treated, solubility characteristics of the neurotoxin toxin chosen as well as the age, sex, weight and health of the patient. For example, the extent of the area of skin influenced is believed to be proportional to the volume of neurotoxin injected, while the quantity of the stretch mark suppressant effect is, for most dose ranges, believed to be proportional to the concentration of a Clostridial toxin administered. Methods for determining the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., 14th edition, published by McGraw Hill).

Significantly, a method within the scope of the present invention can provide improved patient function. "Improved patient function" can be defined as an improvement measured by factors such as a reduced pain, reduced time spent in bed, increased ambulation, healthier attitude, more varied lifestyle and/or healing permitted by normal muscle tone. Improved patient function is synonymous with an improved quality of life (QOL). QOL can be assessed using, for example, the known SF-12 or SF-36 health survey scoring procedures. SF-36 assesses a patient's physical and mental health in the eight domains of physical functioning, role limitations due to physical problems, social functioning, bodily pain, general mental health, role limitations due to emotional problems, vitality and general health perceptions. Scores obtained can be compared to published values available for various general and patient populations.

EXAMPLES

The following non-limiting examples provide those of ordinary skill in the art with specific preferred methods to treat conditions within the scope of the present invention and are not intended to limit the scope of the invention. In the following examples various modes of non-systemic administration of a Clostridial neurotoxin can be carried out. For example, by topical application (cream or transdermal patch), subcutaneous injection, or by implantation of a controlled release implant.

Example 1

Use of a Botulinum Toxin to Treat a Stretch Mark Secondary to Pregnancy

A 29 year old female who recently gave birth can be seen in a dermatology clinic for persistence of stretch marks in the abdominal and breast region, and can desire a treatment to ameliorate the stretch marks. A course of *botulinum* toxin type can be suggested and patient can agree to intradermal injection of a *botulinum* toxin type A. The clinician can apply 25 units of the *botulinum* toxin type A to each of the 5 affected areas: bilateral breast region and lateral flank and abdominal regions for a total of 125 units U (~1 unit/cm2) along dispersed along the stretch marks. About 10 injections/per region or 50 total injections can be administered. Upon follow up 30 days later about 65% of the stretch marks can have resolved with only faint lines present. The patient can return for another course of injections 3 months after her first injections and receive the same amount of *botulinum* toxin type A. Upon subsequent follow up 60 days later all the stretch marks can have had resolved with only 5% faintly present in the abdominal region.

Example 2

Use of a Botulinum Toxin to Treat a Stretch Mark Secondary to Exercise

A 39 year-old body builder weighing 180 pounds can be seen in a dermatology clinic seeking a treatment to resolve stretch marks on his abdominal region. Two years ago, the patient at the time can have weighed 270 pounds and it may be was suggested to him that for health purposes that he reduce his weight through a strict dietary and exercise regime. During this time, the patient can became interested in body building and may have reduced his weight by 90 pounds. As a result of weight lost in the abdominal area that was for years very distended, stretch marks can have become very prominent. To become competitive in body building competition, the patient can want to find a way to remove the unsightly stretch marks. A course of intradermal *botulinum* toxin type A can be was agreed upon and 100 U can be were injected along the path of the stretch marks, 40 injections (2.5 U/0.1 ml) can be applied along the length of the stretch marks. 45 days later the patient can report a significant reduction (about 55% of the stretch marks can have disappeared and the remaining 45% can be only faintly apparent. Another injection session using the same protocol can be applied three months later. Two months following the $2^{nd}$ injection session, the patient can reported complete resolution of the stretch marks.

Example 3

Use of a Botulinum Toxin to Treat a Stretch Mark Secondary to Obesity

A 21 year-old female can be seen in the clinic for treatment of stretch marks in the thigh areas. During adolescence, the patient can have reported a significant weight gain in the thigh region and subsequent formation of stretch marks. By her $20^{th}$ birthday, the patient can have begun to reduce her overall weight from a peak of 160 pounds to a fit 105 pounds. A treatment of 100 U of *botulinum* toxin type can be applied via intra-dermal injection of 5 U/0.1 ml along the surface of the stretch marks, followed by injections of Zyderm I collagen (25% suspension of purified bovine dermis in saline with 0.3% lidocaine) to firm up her thigh region and fill in fine line wrinkles. Upon follow up 2 months later, only faint lines can be observed on the left thigh region and upon second application four months later, the patient can report complete resolution of the stretch marks and firm thigh regions.

In each of the examples above a *botulinum* toxin type B, C, D, E, F or G can be substituted for the *botulinum* toxin type A used above, for example by use of 250 units of a *botulinum* toxin type B. The specific amount of a *botulinum* toxin (such as BOTOX®) administered depends upon a variety of factors to be weighed and considered within the discretion of the attending physician and in each of the examples insignificant amounts of *botulinum* toxin enter appear systemically with no significant side effects.

A method for treating a stretch mark according to the invention disclosed herein has many benefits and advantages, including the following:

1. stretch marks can be dramatically reduced or eliminated.

2. the stretch mark can be reduced or eliminated for at least about two weeks to about six months per injection of neurotoxin and for from about one year to about five years upon use of a controlled release neurotoxin implant.

3. the injected or implanted Clostridial neurotoxin shows little or no tendency to diffuse or to be transported away from the intramuscular (or intradermal or subdermal) injection or implantation site.

4. few or no significant undesirable side effects occur from intramuscular (or intradermal or subdermal) injection or implantation of the Clostridial neurotoxin.

5. the present methods can result in the desirable side effects of greater patient mobility, a more positive attitude and an improved quality of life.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes local administration methods to alleviate a stretch mark wherein two or more neurotoxins, such as two or more *botulinum* toxins, are administered concurrently or consecutively. For example, *botulinum* toxin type A can be administered until a loss of clinical response or neutralizing antibodies develop, followed by administration of *botulinum* toxin type B. Alternately, a combination of any two or more of the *botulinum* serotypes A-G can be locally administered to control the onset and duration of the desired therapeutic result. Furthermore, non-neurotoxin compounds can be administered prior to, concurrently with or subsequent to administration of the neurotoxin to proved adjunct effect such as enhanced or a more rapid onset of denervation before the neurotoxin, such as a *botulinum* toxin, begins to exert its therapeutic effect.

A *botulinum* toxin can be administered by itself or in combination of one or more of the other *botulinum* toxin serotypes. The *botulinum* toxin can be a recombinantly made or a hybrid *botulinum* toxin.

My invention also includes within its scope the use of a neurotoxin, such as a *botulinum* toxin, in the preparation of a medicament for the treatment of a stretch mark, by local administration of the neurotoxin.

All references, articles, patents, applications and publications set forth above are incorporated herein by reference in their entireties.

Accordingly, the spirit and scope of the following claims should not be limited to the descriptions of the preferred embodiments set forth above.

I claim:

1. A method for treating a stretch mark, the method comprising a step of administering a therapeutically effective amount of a *botulinum* toxin to a non-surgically formed stretch mark or to the vicinity of the non-surgically formed stretch mark of a patient seeking treatment of the stretch mark, thereby treating the stretch mark.

2. The method of claim 1, wherein the *botulinum* toxin is selected from the group consisting of *botulinum* toxin types A, B, C, D, F, F and G.

3. The method of claim 1, wherein the *botulinum* toxin is a *botulinum* toxin type A.

4. The method of claim 1, wherein the administration is by intradermal administration of the *botulinum* toxin.

5. A method for treating a stretch mark, the method comprising the step of locally administering a therapeutically effective amount of a *botulinum* toxin to a non-surgically formed stretch mark, thereby treating the stretch mark.

6. The method of claim 5, wherein treating the stretch mark reduces at least one of pain associated with the stretch mark, inflammation associated with the stretch mark, and the size or visibility of the stretch mark.

7. The method of claim 1, wherein administering the *botulinum* toxin is effective in preventing the release of at least one neuropeptide selected from the group consisting of tachykinins, substance P, neurokinin A, calcitonin gene-related peptide, vasoactive intestinal peptide and somatostatin, released by a nerve that innervates the skin of the patient.

8. The method of claim 7, wherein administering the *botulinum* toxin is effective in inhibiting release of at least one of calcitonin gene related peptide, substance P, and glutamate from dermal sensory nerves.

9. The method of claim 1, wherein administering the *botulinum* toxin is effective in treating a stretch mark associated with a condition selected from the group consisting of pregnancy, lactation, obesity and weight lifting.

10. The method of claim 1, wherein the *botulinum* toxin is administered to a stretch mark resulting from excessive mast cell degranulation.

11. The method of claim 1, wherein the *botulinum* toxin administered to a stretch mark occurring in the dermis of the patient and resulting from skin distension, or to the vicinity of the stretch mark.

* * * * *

UNITED STATES PATENT AND TRADEMARK OFFICE
CERTIFICATE OF CORRECTION

PATENT NO. : 7,429,386 B2
APPLICATION NO. : 10/934812
DATED : September 30, 2008
INVENTOR(S) : Eric R. First It is certified that error appears in the above-identified patent and that said Letters Patent is hereby corrected as shown below:

On the face page, in field (56), under "Other Publications", in column 2, line 23, delete "2005;92" and insert -- 1995;92 --, therefor.

On page 2, in field (56), under "Other Publications", in column 1, line 11, delete "fo" and insert -- of --, therefor.

On page 2, in field (56), under "Other Publications", in column 2, line 23, delete "glutamute" and insert -- glutamate --, therefor.

On page 2, in field (56), under "Other Publications", in column 2, line 31, delete "noradenaline," and insert -- noradrenaline, --, therefor.

On page 3, in field (56), under "Other Publications", in column 1, line 23, delete "Glutamine" and insert -- Glutamate --, therefor.

On page 3, in field (56), under "Other Publications", in column 2, line 2, after "weeks" insert -- before --.

On page 3, in field (56), under "Other Publications", in column 2, line 4, delete "Pharamcological" and insert -- Pharmacological --, therefor.

On page 3, in field (56), under "Other Publications", in column 2, line 18, after "line" insert -- in --.

On page 3, in field (56), under "Other Publications", in column 2, line 25, delete "immunoshistochemical" and insert -- immunohistochemical --, therefor.

UNITED STATES PATENT AND TRADEMARK OFFICE
CERTIFICATE OF CORRECTION

PATENT NO.         : 7,429,386 B2
APPLICATION NO. : 10/934812
DATED              : September 30, 2008
INVENTOR(S)        : Eric R. First It is certified that error appears in the above-identified patent and that said Letters Patent is hereby corrected as shown below:

On page 3, in field (56), under "Other Publications", in column 2, line 32, after "GB;" insert -- Class B04, --.

Signed and Sealed this

First Day of September, 2009

David J. Kappos
*Director of the United States Patent and Trademark Office*